US010301055B2

(12) United States Patent
Ibarreche Fonseca et al.

(10) Patent No.: US 10,301,055 B2
(45) Date of Patent: May 28, 2019

(54) DOSING SYSTEM

(71) Applicant: Andrés Fernando González Sierra, Bogotá (CO)

(72) Inventors: Elena Ibarreche Fonseca, Bogotá (CO); Danny Bohórquez Montenegro, Bogotá (CO); Alvaro Leo Dan Gómez Muñoz, Bogotá (CO)

(73) Assignee: Andres Fernando Gonzalez Sierra, Bogota (CO)

( * ) Notice: Subject to any disclaimer, the term of this patent is extended or adjusted under 35 U.S.C. 154(b) by 0 days.

(21) Appl. No.: 15/314,908

(22) PCT Filed: Mar. 30, 2016

(86) PCT No.: PCT/IB2016/051809
§ 371 (c)(1),
(2) Date: Nov. 29, 2016

(87) PCT Pub. No.: WO2016/198967
PCT Pub. Date: Dec. 15, 2016

(65) Prior Publication Data
US 2018/0111713 A1 Apr. 26, 2018

(30) Foreign Application Priority Data

Jun. 9, 2015 (CO) .................... 15131814

(51) Int. Cl.
*B65D 1/08* (2006.01)
*B65D 47/18* (2006.01)
(Continued)

(52) U.S. Cl.
CPC ................ *B65D 1/08* (2013.01); *A61F 9/00* (2013.01); *A61J 1/1412* (2013.01); *A61J 1/1443* (2013.01);
(Continued)

(58) Field of Classification Search
CPC ........ B65D 1/08; B65D 47/18; B65D 47/122; B65D 41/3409; B65D 2101/0038;
(Continued)

(56) References Cited

U.S. PATENT DOCUMENTS 2,240,329 A * 4/1941 Fialip ..................... B65D 47/18
222/209
3,269,617 A * 8/1966 Goth .................. B65D 47/0842
215/41
(Continued)

FOREIGN PATENT DOCUMENTS

JP 56145346 U 3/1986
KR 10-1415854 B1 7/2014
WO WO 01/046035 A1 6/2001

OTHER PUBLICATIONS

WIPO Application No. PCT/IB2016/051809, International Search Report, dated Jul. 6, 2016.
(Continued)

*Primary Examiner* — Paul R Durand
*Assistant Examiner* — Andrew P Bainbridge
(74) *Attorney, Agent, or Firm* — Schwabe, Williamson & Wyatt PC

(57) ABSTRACT

The present invention refers to an improved dispensing system for liquid dispensing in the form of drops, comprising: a cap; a dosage unit having a skirt showing a protrusion or edge at its lower end; and a container having a shoulder surface located at the inner part of the shoulder, wherein the shoulder surface holds the dosage unit through interfering with said protrusion or edge of the insert thus avoiding that the dosage unit can be removed from the container. While opening the improved dispensing system according to the present invention, a ring attached to the cap body breaks in sections, preventing said ring to be relocated in the cap and,
(Continued)

thus, avoiding that the dosage unit can be reused for filling a different substance.

20 Claims, 9 Drawing Sheets

(51) Int. Cl.
  *A61J 1/14* (2006.01)
  *A61F 9/00* (2006.01)
  *B65D 41/34* (2006.01)
  *B65D 47/12* (2006.01)

(52) U.S. Cl.
  CPC ......... *B65D 41/3409* (2013.01); *B65D 47/18* (2013.01); *A61J 1/1475* (2013.01); *B65D 47/122* (2013.01); *B65D 2101/0038* (2013.01)

(58) Field of Classification Search
  CPC ..... B65D 47/248; A61J 1/1412; A61J 1/1443; A61J 1/1475; A61F 9/00; B01L 3/0265
  USPC ...... 222/153.05–153.06, 153.09–153.1, 542, 222/17, 562–563, 573, 570, 420–422, 222/541.1–541.9, 566–568
  See application file for complete search history.

(56) References Cited

U.S. PATENT DOCUMENTS

| | | | | |
|---|---|---|---|---|
| 4,231,486 A | * | 11/1980 | Bock | B65D 21/0219 220/266 |
| 4,305,516 A | * | 12/1981 | Perne | B65D 41/3442 215/252 |
| 4,651,885 A | * | 3/1987 | Gach | B65D 51/20 215/250 |
| 5,065,908 A | * | 11/1991 | Mengeu | B65D 47/06 215/355 |
| 5,373,964 A | * | 12/1994 | Moore | A61F 9/0008 222/1 |
| 6,161,711 A | * | 12/2000 | Miceli | B65D 50/061 215/206 |
| 6,357,628 B1 | * | 3/2002 | Long, Jr. | B65D 41/3447 222/153.06 |
| 6,394,323 B2 | * | 5/2002 | McClean | B65D 47/0838 215/235 |
| 6,631,820 B2 | * | 10/2003 | Harrold | B65D 47/0809 215/230 |
| 6,632,202 B1 | * | 10/2003 | Hagele | A61F 9/0008 222/420 |
| 6,981,600 B1 | * | 1/2006 | Battegazzore | B65D 41/3442 215/230 |
| 7,178,703 B2 | * | 2/2007 | Spada | A61F 9/0008 222/209 |
| 7,303,098 B2 | * | 12/2007 | Backes | B65D 47/18 222/212 |
| 7,635,071 B1 | | 12/2009 | Montgomery et al. | |
| 8,408,433 B2 | * | 4/2013 | Fontana | B65D 47/2068 222/107 |
| 8,444,610 B2 | * | 5/2013 | Grevin | A61F 9/0008 222/420 |
| D684,057 S | * | 6/2013 | Kwon | D9/453 |
| 9,533,802 B2 | * | 1/2017 | Berge | B65D 47/12 |
| 9,908,666 B2 | * | 3/2018 | Walsh | B65D 39/08 |
| 2004/0050881 A1 | * | 3/2004 | Deussen | B65D 47/18 222/420 |
| 2006/0032873 A1 | | 2/2006 | Gerondale et al. | |
| 2006/0037968 A1 | * | 2/2006 | Brenner | B65D 47/2075 222/105 |
| 2010/0213213 A1 | * | 8/2010 | Albers | B65D 41/3409 222/153.05 |
| 2013/0277328 A1 | * | 10/2013 | Hindle | B65D 41/62 215/200 |
| 2014/0291360 A1 | * | 10/2014 | Bracha | B65D 47/122 222/568 |
| 2015/0166229 A1 | * | 6/2015 | Wochele | B65D 41/48 222/153.05 |
| 2018/0111713 A1 | * | 4/2018 | Ibarreche Fonseca | A61F 9/00 |

OTHER PUBLICATIONS

WIPO Application No. PCT/IB2016/051809, Written Opinion of the International Searching Authority, dated Jul. 6, 2016, machine translation of Cites and Explanations on pp. 2-3.

* cited by examiner

DOSING SYSTEM

CROSS-REFERENCE TO RELATED APPLICATIONS

This application is a US national stage of International Application No. PCT/IB2016/051809, filed Mar. 30, 2016, which claims the benefit of Colombian Application No. 15131804, filed Jun. 9, 2015, which is herein specifically incorporated by reference in its entirety.

FIELD OF THE INVENTION

The present invention relates to the field of containers that allow a controlled dosing or individual drop dosage, more particularly, the invention refers to a system comprising a container having a tamper evident safety cap and a non-refillable tamper proof dosage unit which does not allow to be reusable.

BACKGROUND OF THE INVENTION

In the field of containers for liquid products there has been the need for developing containers that allow evidencing the aperture or tampering thereof which is known in this area as "tamper evident" in order to offer the final consumer the confidence that the container has not been previously opened, and that its content has not been altered.

Also, recently, there has been the need for producing containers that do not allow the final user to manipulate it, for example, reusing the container for a different purpose. In particular, it has been observed that final consumers of the product contained in the container, are frequently reusing the container by removing the dosage element from the container or bottle and refilling the container with a different substance.

Such container reutilization practice has various undesirable consequences but mainly, causes that an unaware user thinks that the content of the container is the originally liquid which can cause an accident through the administration of a wrong liquid to a patient, for example, assuming that the original liquid is being dispensed.

There are in the market various types of containers having dosage units for eyedroppers and having tamper evident caps. For example, the Colombian patent application 11-145696 shows a cap assembly, eyedropper insert having a tamper evident mechanism, wherein a collar is detached when the cap is opened. But, this invention does not include a mechanism preventing the container to be refilled with another liquid once the product has been opened.

Also, patent publication WO 2006/0585011A1 discloses a container having a cap and an eyedropper insert. This publication does neither provide a tamper evident mechanism nor a mechanism for preventing the container to be reused.

Facing this problem, it is necessary to develop containers for containing liquid products that not only have a system that allows evidencing the opening or manipulation for the final consumer safety, but also includes a mechanism the prevents the reutilization of the container, for example preventing the removal of the eyedropper insert, thus avoiding, or at least making more difficult refilling the container.

DESCRIPTION OF THE INVENTION

The present invention consists in an improved dispensing system for liquid dispensing in the form of drops, comprising a cap; a dosage unit having a skirt showing a protrusion or edge; and a container having a shoulder surface located at the inner part of the shoulder; wherein, the shoulder surface holds the dosage unit through the interference of said protrusion or edge with the dosage unit.

While opening the dispensing system according to the present invention, a ring attached to the cap body breaks in sections, preventing said ring to be again located in the cap and, thus, evidencing that the dispensing system of the invention was previously opened.

BRIEF DESCRIPTION OF THE FIGURES

The present description is complemented with a set of illustrative drawings of the preferred and non-limitative examples of the invention.

LIST OF THE ELEMENTS OF THE INVENTION

Figure 1:
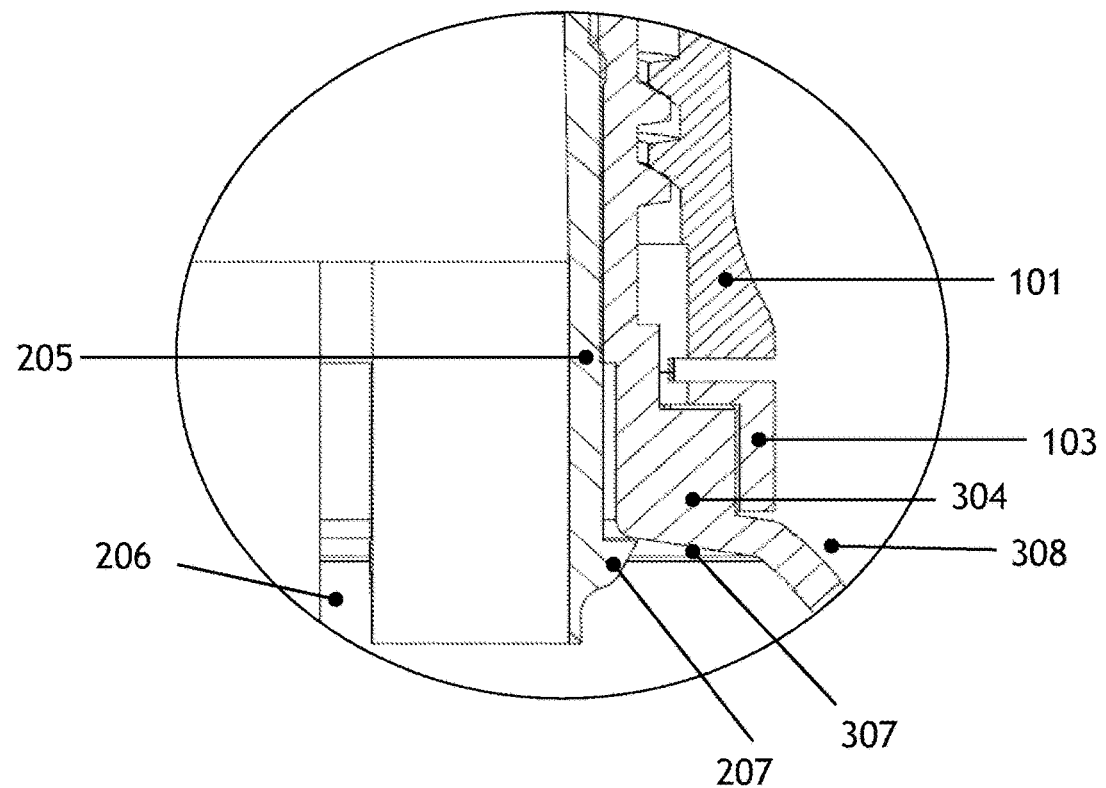
FIG. 1 shows a magnified cross section view of the improved dispensing system (500).

500 Dispensing system
100 Cap
101 Cap body
102 Slots
103 Ring
104 Fins
105 Annular cut
106 inner thread
107 inner ring
108 ring projection
109 binding points
200 Dosage unit
201 dosage portion
202 Protrusion
203 Adjustment surface
204 Retaining ring
205 Skirt
206 Adjustment aperture
207 protrusion or edge
208 Channel
209 Positioning portion
300 Container
301 Container body
302 Container opening
303 Inscription/warning
304 Ratchet
305 Thread
306 Container retaining ring
307 Shoulder surface
308 Shoulder
309 Container neck

DETAILED DESCRIPTION OF THE INVENTION

The present invention consists in a dispensing system (500) for liquid dispensing in the form of drops which comprises a cap (100), a dosage unit (200) having a skirt (205) showing a protrusion or edge (207) at its lower end and a container (300) having a shoulder surface (307) located at the inner part of the shoulder (308), wherein the shoulder surface (307) holds the dosage unit (200) through the interference of said protrusion or edge (207) with the dosage unit (200).

Figure 2:
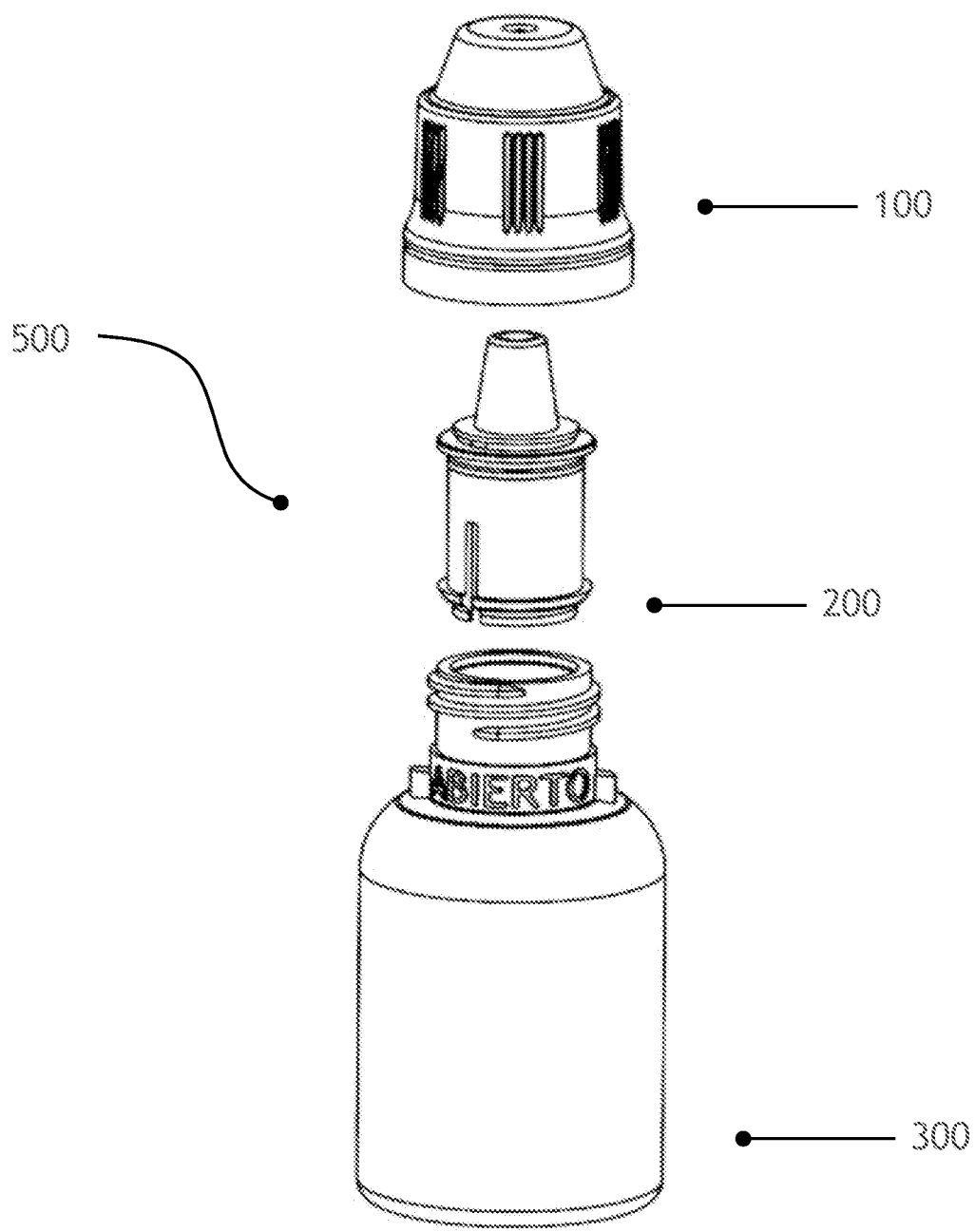
FIG. 2 shows an explosion view of the improved dispensing system (500) according to the invention.

The explosion view of the elements of the dispensing system (500) of the invention can be seen in FIG. 2.

Figure 3:
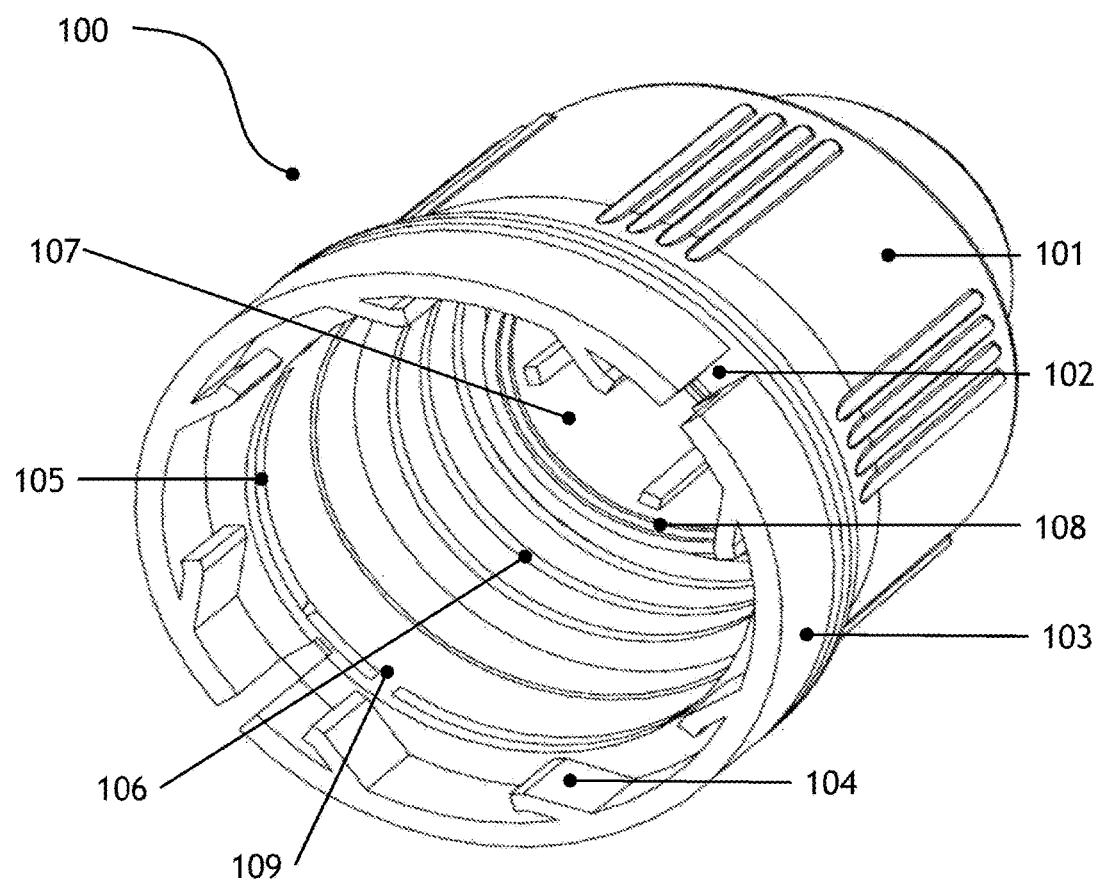
FIG. 3 shows a bottom view of the cap (100) wherein the elements forming same are detailed.

As can be seen in FIG. 3, the cap (100) is provided with an inner ring (107), a ring projection (108) of the inner ring (107), a ring (103) attached to the cap body (101) through a plurality of binding points (109) radially located on ring (103), fins (104) located in the inner part of the ring (103) and slots (102) perpendicularly located on the ring (103).

Figure 4:
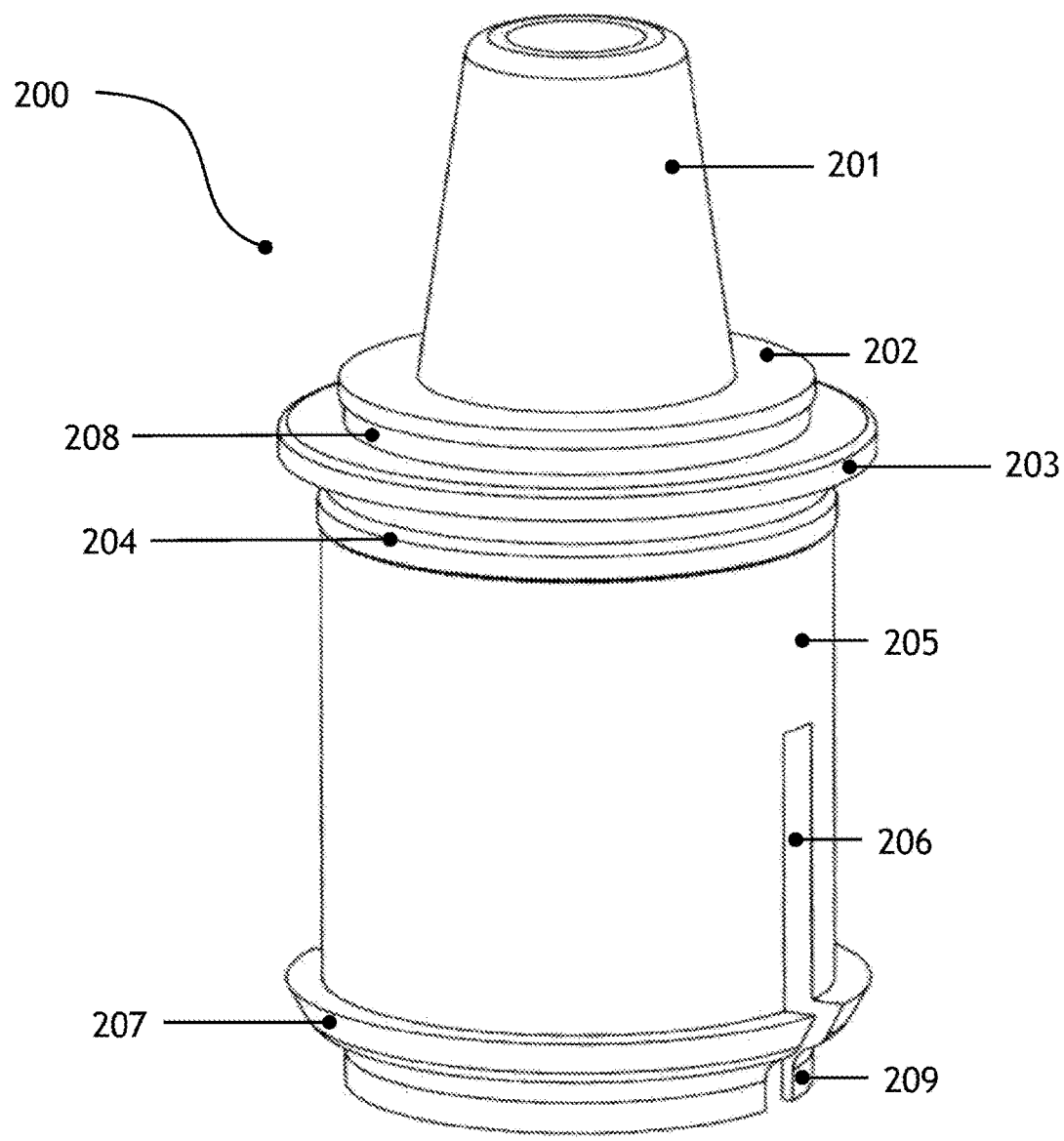
FIG. 4 shows a front view of the dosage unit (200), wherein the elements forming same are detailed.

As can be observed in FIG. 4, the dosage unit (200) comprises a dosage portion (201) located on the upper segment of the dosage unit (200), a protrusion (202) located at the lower part of the dosage portion (201), an adjustment surface (203) located between the dosage portion (201) and a skirt (205) of the dosage unit (200).

The dosage unit (200) further comprises a retaining ring (204), an adjustment aperture (206), a protrusion or edge (207) located at the lower part of the skirt (205), a channel (208) and a positioning portion (209) located at the lower part of the dosage unit (200) immediately below the protrusion or edge (207).

Figure 5:
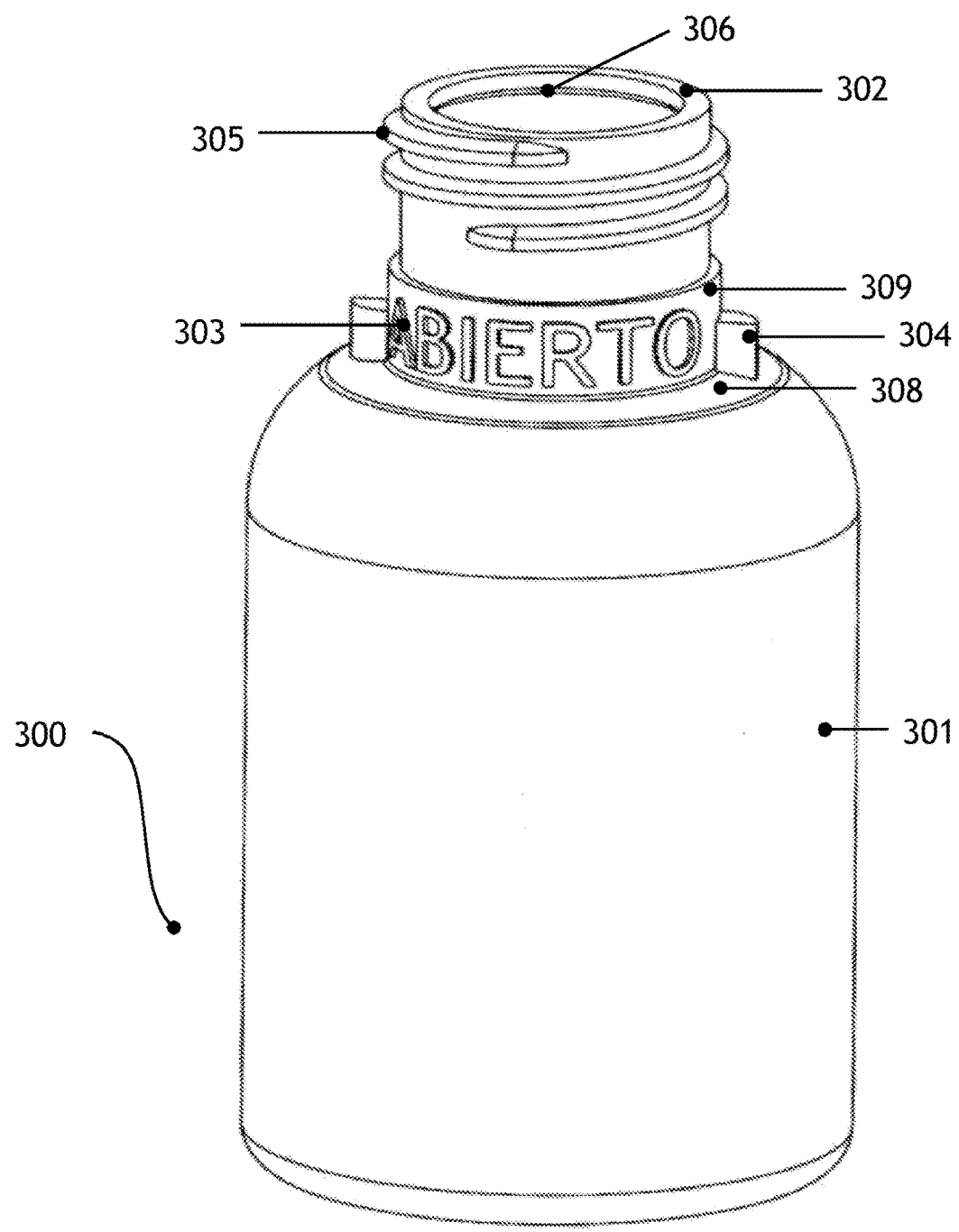
FIG. 5 shows a front view of container (300).

According to FIG. 5, the container (300) is provided with a thread (305) located on the outer part or the container opening (302), a container retaining ring (306) (shown in FIG. 7), located at the inner part of the container opening (302), ratchets (304) located at the outer part of the container neck (309), a surface (307) (Shown in FIG. 1 and FIG. 7), located at the inner part of container (300) and radially extending over the shoulder (308).

Figure 6:
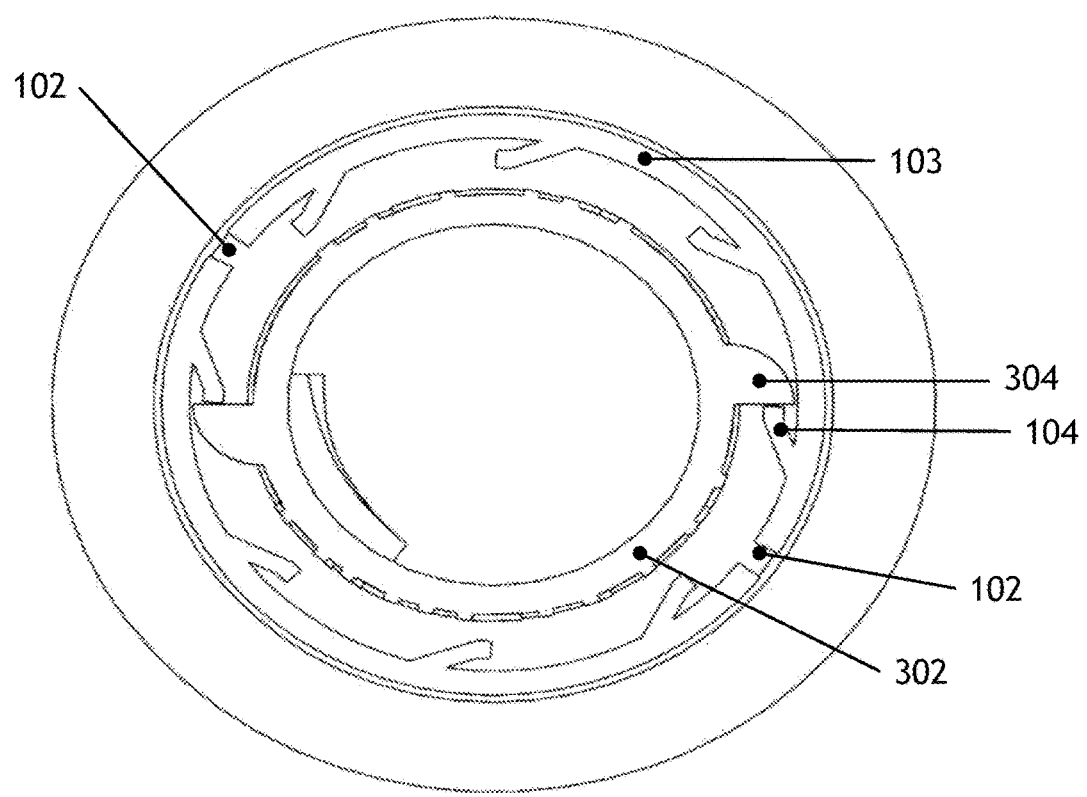
FIG. 6 shows a bottom view of the cap (100).

In the aperture operation of dispensing system (500), the fins (104) of the cap (100) face the ratchets (304) of the container (300) when the cap (100) rotates, causing ring (103) to detach from the cap body (101) along the annular cut (105) and the bindings between the semi-rings forming the ring break, due to shearing of the binding points (109) and finally, the ring (103) is divided in sections according to the slots (102), see FIG. 6).

Figure 7:
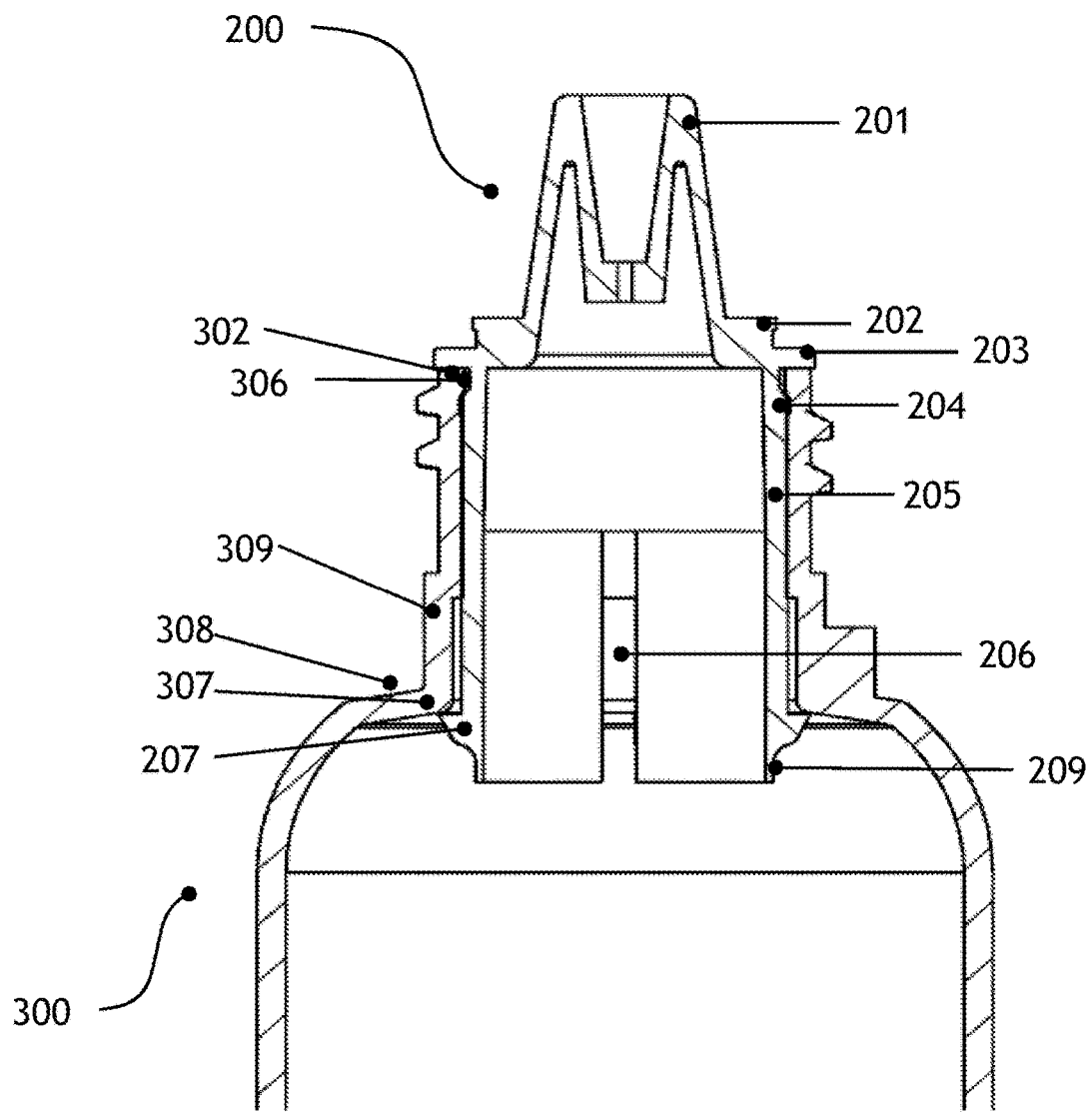
FIG. 7 shows a cross-section view of the dosage unit (200) assembled in the container (300).

During the dosage unit (200) assembling onto the container (300) as seen in FIG. 7, once the container (300) has been filled with the desired liquid, the dosage unit (200) is fixedly/inseparably embedded in container (300) when it slides through the container opening (302) and along the container neck (309) which is possible by the adjustment aperture (206) contraction until the protrusion or edge (207) of the dosage unit (200) exceeds surface (307) of container (300) thus obtaining a safe assembly of the dosage unit (200) in the container (300) as the protrusion or edge (207) remains secured against the container neck (309).

Figure 8:
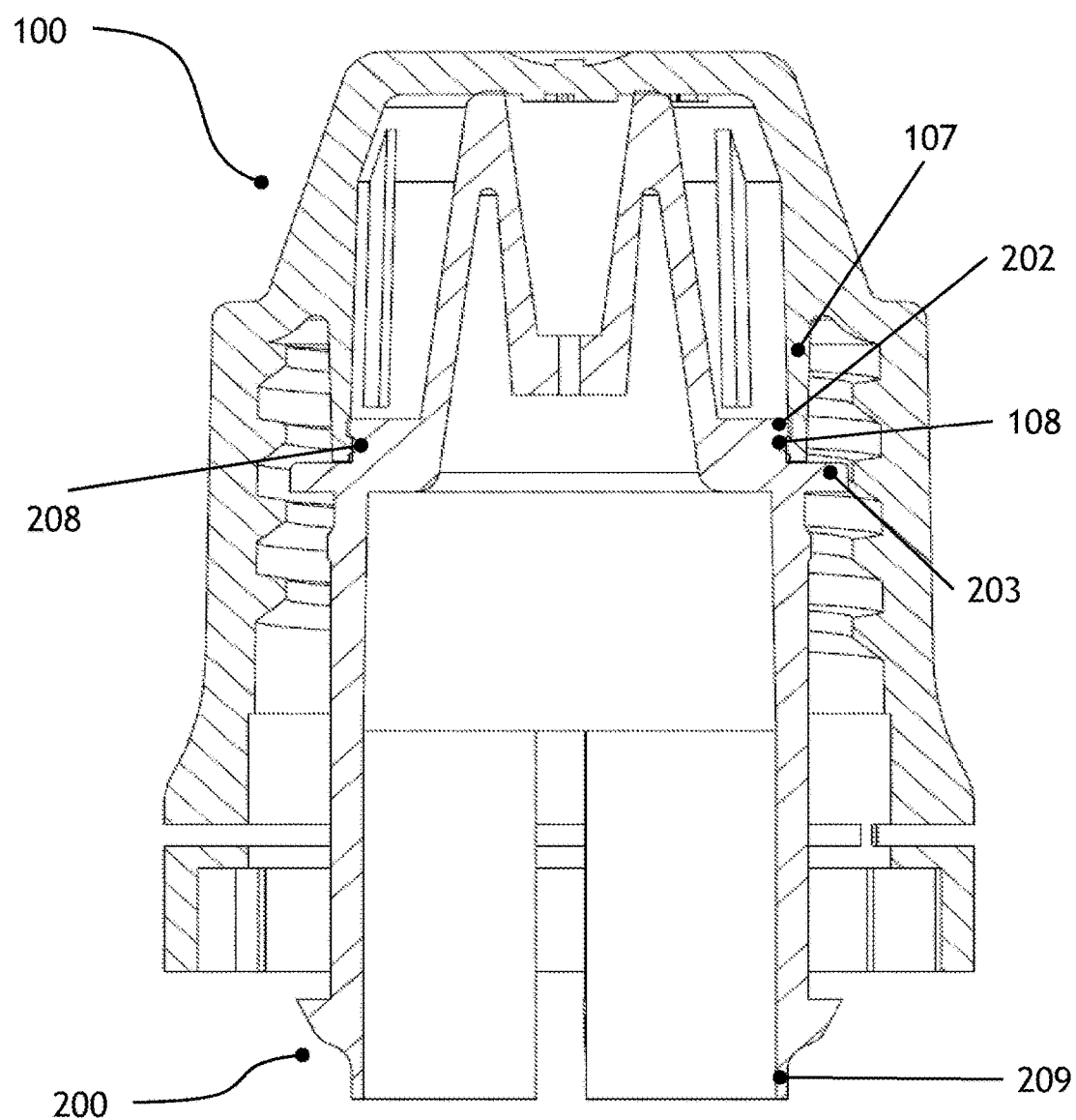
FIG. 8 shows a cross-section view of pre-assembled cap assembly (100) and dosage unit (200), prior to be attached to the container (300).

According to FIG. 8, the dosage unit (200) is fitted in the cap (100) through the connection between the ring projection (108) of the cap, within the channel (208) located beneath the protrusion (202) in the dosage unit (200).

Assembling the cap (100), the dosage unit (200) and the container (300) can be carried out through initially pre-assembling the dosage unit (200) into the cap (100), then locate this pre-assembled unit over the neck (309) of the container (300) and closing using the thread (305) and the inner thread (106).

Figure 9:
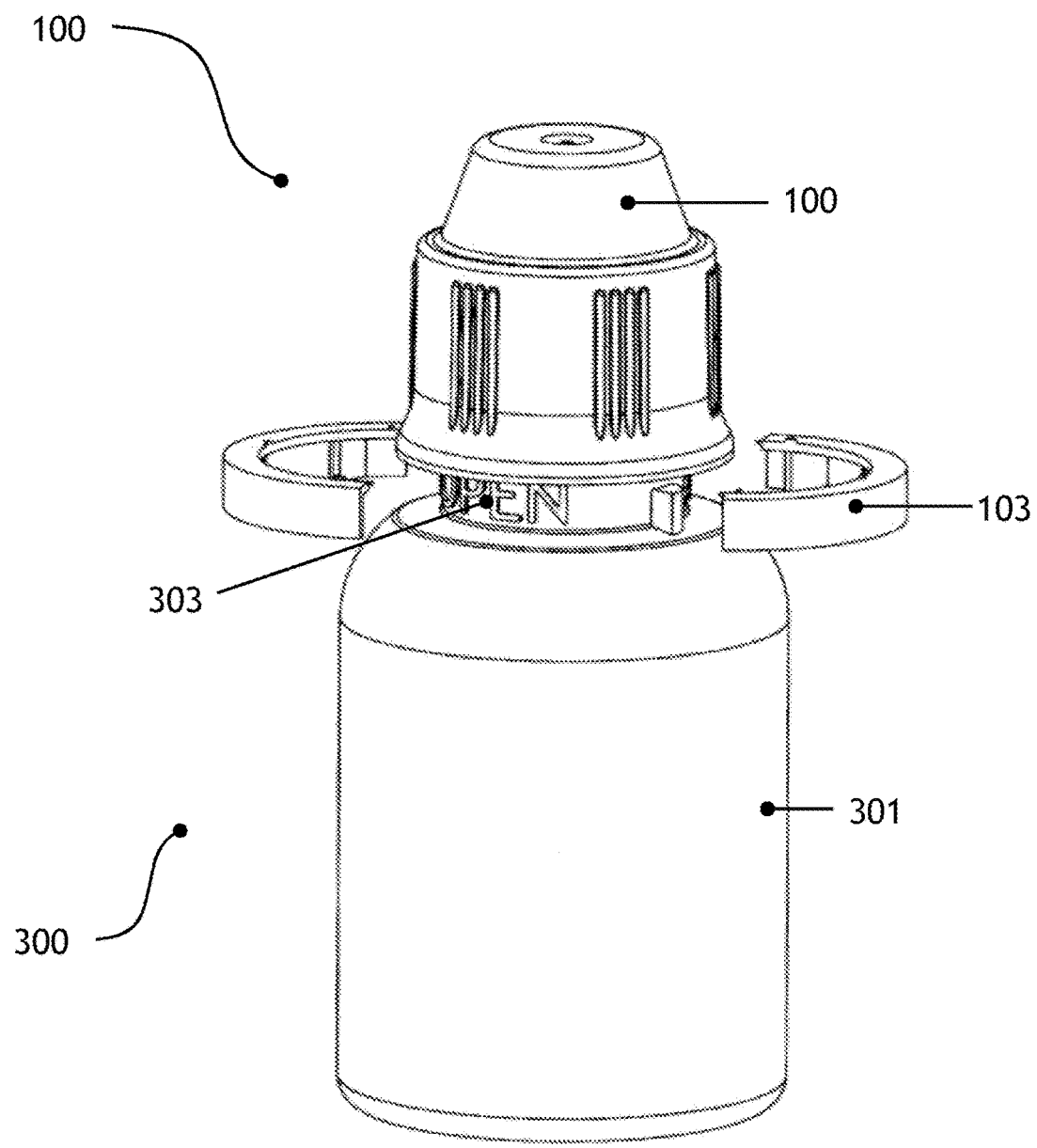
FIG. 9 shows a detail of the ring system which allows evidencing the manipulation of the cap (100).

During the aperture of the dispenser (500), the ring (103) definitively breaks into sections, preventing said ring (103) to be relocated in the cap (100) as can be seen in FIG. 9 of the invention.

The container (300) may further have an inscription or warning label (303) located at the outer lower part of the container opening (302) such that when ring (103) is released or detached by removing the cap for the first time, said warning (303) becomes visible to the eyes of the consumer, advising him/her that said container has been opened. See FIG. 9.

Other embodiments of the present invention evident to those skilled in the art after the description of the present invention has been read and the invention practiced, are understood to be included within the scope of protection of the present invention. The present description is illustrative and not limitative of the scope and spirit of the invention, which is only limited by the following claims.

The invention claimed is:

1. An improved dispensing system, comprising:
   a cap that includes a threaded portion and comprises:
   an inner ring;
   a ring projection of the inner ring;
   a second ring attached to a cap body through binding points;
   fins located at an inner part of the second ring; and
   slots perpendicularly located in the second ring;
   a dosage unit, having a constant diameter skirt with a protrusion or edge extending from a lower end of the skirt; and
   a container having a constant diameter neck and a surface located at an inner part of a shoulder extending from the neck, wherein the surface is configured to hold the dosage unit in the container through interference with the protrusion or edge of the dosage unit.

2. The improved dispensing system according to claim 1 wherein the second ring has divisions according to a location of the slots.

3. The improved dispensing system according to claim 1, wherein the dosage unit comprises a frustoconical-shaped upper element, wherein the skirt has two side adjustment apertures, and the protrusion or edge has a ratchet tooth profile located in the lower part of the skirt, wherein the frustoconical element lays over a washer which is an integral part of the frustoconical element and the skirt of the dosage unit; a retaining ring, a channel located between adjustment protrusion or edge and the washer of the frustoconical element, wherein said frustoconical element corresponds to a dosage nozzle.

4. The improved dispensing system according to claim 3, wherein the container further has an inscription or warning located at the lower outer part of the container opening.

5. The improved dispensing system according to claim 1 wherein the container comprises:
   a thread located at an outer part of an opening of the container;
   a container retaining ring, located at an inner part the opening of the container;
   ratchets located at an outer part of the container neck;
   and wherein the surface is located at the inner part of the container and radially extends along the inside of the shoulder.

6. The improved dispensing system according to claim 1, wherein the fins of the cap are facing ratchets of the container when the cap rotates, and the second ring is detached from the cap body along an annular cut due to the binding points shearing and where the second ring is divided into sections according to the slots.

7. The improved dispensing system according to claim 6 wherein after the dispensing system has been opened, the second ring breaks in sections, preventing said second ring to be relocated in the cap.

8. The improved dispensing system according to claim 1 wherein the dosage unit is embedded into the container when sliding through an opening of the container and along the container neck which is possible due to the contraction of adjustment apertures in the skirt until the protrusion or edge of the dosage unit exceeds the surface of container as the protrusion or edge remains secured against the container neck.

9. The improved dispensing system according to claim 1 wherein the dosage unit fits into the cap through a connection between the ring projection of the inner ring of the cap, within a channel located beneath a washer of the dosage unit allowing pre-assembling the dosage unit.

10. The improved dispensing system according to claim 9 wherein assembling the cap, the dosage unit and the container is carried out through locating the pre-assembled unit of the dosage unit and the cap over the neck of the container and closing using the cap thread and an inner container thread.

11. An improved dispensing system, comprising:
a cap;
a dosage unit, having a constant diameter skirt and an frustoconical-shaped upper element, wherein the skirt has two side adjustment apertures, a protrusion or edge having a ratchet tooth profile located in the lower part of the skirt, wherein the frustoconical element lays over a washer which is an integral part of the frustoconical element and the skirt of the dosage unit; a retaining ring; a protrusion or edge located at the lower part of the skirt, a channel located between the adjustment protrusion or edge and the washer of the frustoconical element, wherein said frustoconical element correspond to a dosage nozzle; and
a container having a constant diameter neck and a surface located at an inner part of a shoulder extending from the neck, wherein the surface is configured to hold the dosage unit in the container through interference with the protrusion or edge of the dosage unit.

12. The improved dispensing system according to claim 11 wherein the container further has an inscription or warning located at the lower outer part of the container opening.

13. The improved dispensing system according to claim 11 wherein the container comprises:
a thread located at the outer part of an opening of the container;
a container retaining ring, located at the inner part of the opening of the container;
ratchets located at the outer part of the container neck;
and wherein the surface is located at the inner part of the container and radially extends along the inside of the shoulder.

14. The improved dispensing system according to claim 11 wherein the cap includes a threaded portion and comprises:
an inner ring;
a ring projection of the inner ring;
a second ring attached to a cap body through binding points;
fins located at an inner part of the second ring; and
slots perpendicularly located in the second ring.

15. The improved dispensing system according to claim 14, wherein the second ring has divisions according to a location of the slots.

16. The improved dispensing system according to claim 14, wherein the fins of the cap are facing ratchets of the container when the cap rotates, and the second ring is detached from the cap body along an annular cut due to the binding points shearing and where the second ring is divided into sections according to the slots.

17. The improved dispensing system according to claim 16, wherein after the dispensing system has been opened, the second ring breaks in sections, preventing said second ring to be relocated in the cap.

18. The improved dispensing system according to claim 11, wherein the dosage unit is embedded into the container when sliding through a container opening and along the container neck which is possible due to the contraction of adjustment apertures until the protrusion or edge of the dosage unit exceeds surface of container as the protrusion or edge remains secured against the container neck.

19. The improved dispensing system according to claim 11, wherein the dosage unit fits into the cap through a connection between the ring projection of the inner ring of the cap, within a channel located beneath a washer of the dosage unit allowing pre-assembling the dosage unit.

20. The improved dispensing system according to claim 19, wherein assembling cap, dosage unit and container is carried out through locating the pre-assembled unit of the dosage unit and the cap over the neck of container and closing using the thread and the inner thread.

* * * * *